US008679109B2

(12) United States Patent  
Paul et al.

(10) Patent No.: US 8,679,109 B2  
(45) Date of Patent: Mar. 25, 2014

(54) DYNAMIC CONTACT ASSESSMENT FOR ELECTRODE CATHETERS

(75) Inventors: Saurav Paul, Minnetonka, MN (US); Chou Thao, Brooklyn Park, MN (US); Kedar Ravindra Belhe, Minnetonka, MN (US); Reed R. Heimbecher, Hamel, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1402 days.

(21) Appl. No.: 11/549,100

(22) Filed: Oct. 12, 2006

(65) Prior Publication Data

US 2008/0015568 A1    Jan. 17, 2008

Related U.S. Application Data

(60) Provisional application No. 60/727,164, filed on Oct. 13, 2005.

(51) Int. Cl.  
*A61B 18/18* (2006.01)

(52) U.S. Cl.  
USPC ............................................. 606/41; 606/45

(58) Field of Classification Search  
USPC ...................................................... 606/32–45  
See application file for complete search history.

(56) References Cited

U.S. PATENT DOCUMENTS

| | | | |
|---|---|---|---|
| 4,600,017 A | 7/1986 | Schroeppel | |
| 4,682,596 A | 7/1987 | Bales et al. | |
| 4,799,495 A | 1/1989 | Hawkins et al. | |
| 4,911,174 A | 3/1990 | Pederson et al. | |
| 4,976,711 A | 12/1990 | Parins et al. | |
| 4,991,588 A | 2/1991 | Pflueger et al. | |
| 5,028,394 A | 7/1991 | Lowell, Jr. et al. | |
| 5,341,807 A | 8/1994 | Nardella | |
| 5,354,279 A | 10/1994 | Höfling | |
| 5,372,603 A | 12/1994 | Acker et al. | |
| 5,405,346 A | 4/1995 | Grundy et al. | |
| 5,447,529 A | 9/1995 | Marchlinski | |
| 5,536,245 A * | 7/1996 | Dahlbeck ...................... 600/195 |

(Continued)

FOREIGN PATENT DOCUMENTS

EP             1491139          12/2004  
WO     WO2005039835      5/2005

OTHER PUBLICATIONS

PCT International Search Report and Written Opinion of the International Searching Authority for PCT/US06/39881, dated Jun. 30, 2008, 7 pages.

(Continued)

*Primary Examiner* — Linda Dvorak  
*Assistant Examiner* — Amanda Scott  
(74) *Attorney, Agent, or Firm* — Trenner Law Firm, LLC

(57) ABSTRACT

An electrode catheter and a method for assessing catheter-tissue contact for tissue ablation are disclosed. An exemplary electrode catheter comprises a flexible catheter shaft. At least one piezoelectric sensor is oriented coaxial to the flexible catheter shaft. The at least one piezoelectric sensor is responsive to movement of the flexible catheter shaft by generating electrical signals corresponding to the amount of movement. The system may also include an output device electrically connected to the at least one piezoelectric sensor. The output device receives the electrical signals for dynamically assessing a level of contact between the flexible catheter shaft and a moving tissue. In another exemplary embodiment, the system may be implemented in a hydrodynamic environment.

34 Claims, 13 Drawing Sheets

(56) References Cited

U.S. PATENT DOCUMENTS

| | | | |
|---|---|---|---|
| 5,643,197 | A | 7/1997 | Brucker et al. |
| 5,697,925 | A | 12/1997 | Taylor |
| 5,782,828 | A | 7/1998 | Chen et al. |
| 5,836,990 | A | 11/1998 | Li |
| 5,868,737 | A | 2/1999 | Taylor et al. |
| 5,893,848 | A * | 4/1999 | Negus et al. .................... 606/41 |
| 5,895,355 | A | 4/1999 | Schaer |
| 5,947,905 | A | 9/1999 | Hadjicostis et al. |
| 6,013,074 | A | 1/2000 | Taylor |
| 6,039,731 | A | 3/2000 | Taylor et al. |
| 6,066,139 | A | 5/2000 | Ryan et al. |
| 6,078,830 | A | 6/2000 | Levin et al. |
| 6,113,592 | A | 9/2000 | Taylor |
| 6,113,593 | A | 9/2000 | Tu et al. |
| 6,127,672 | A | 10/2000 | Danisch |
| 6,171,304 | B1 | 1/2001 | Netherly et al. |
| 6,210,406 | B1 | 4/2001 | Webster |
| 6,217,573 | B1 | 4/2001 | Webster |
| 6,217,574 | B1 | 4/2001 | Webster |
| 6,241,724 | B1 | 6/2001 | Fleischman et al. |
| 6,246,898 | B1 | 6/2001 | Vesely et al. |
| 6,264,653 | B1 | 7/2001 | Falwell |
| 6,272,371 | B1 | 8/2001 | Shlomo |
| 6,304,776 | B1 | 10/2001 | Muntermann |
| 6,322,558 | B1 | 11/2001 | Taylor et al. |
| 6,325,799 | B1 | 12/2001 | Goble |
| 6,391,024 | B1 | 5/2002 | Sun et al. |
| 6,423,057 | B1 | 7/2002 | He et al. |
| 6,470,236 | B2 | 10/2002 | Ohtsuki |
| 6,696,844 | B2 | 2/2004 | Wong et al. |
| 6,800,986 | B2 | 10/2004 | Yamauchi |
| 6,837,886 | B2 | 1/2005 | Collins et al. |
| 6,845,264 | B1 | 1/2005 | Skladnev et al. |
| 6,882,885 | B2 | 4/2005 | Levy, Jr. et al. |
| 7,011,410 | B2 | 3/2006 | Bolger et al. |
| 7,060,965 | B2 | 6/2006 | Vidovic et al. |
| 2001/0034501 | A1 | 10/2001 | Tom |
| 2002/0123749 | A1 | 9/2002 | Jain |
| 2003/0204184 | A1 | 10/2003 | Ferek-Patric |
| 2004/0199156 | A1 | 10/2004 | Rioux et al. |
| 2004/0210214 | A1 | 10/2004 | Knowlton |
| 2005/0159739 | A1 | 7/2005 | Paul et al. |
| 2005/0159741 | A1 | 7/2005 | Paul et al. |
| 2005/0267467 | A1 | 12/2005 | Paul et al. |
| 2007/0078484 | A1 * | 4/2007 | Talarico et al. ................ 606/205 |
| 2008/0255629 | A1 | 10/2008 | Jenson et al. |
| 2008/0275442 | A1 * | 11/2008 | Paul et al. ....................... 606/41 |
| 2009/0158852 | A1 * | 6/2009 | Paul et al. ....................... 73/723 |

OTHER PUBLICATIONS

PCT International Search Report and Written Opinion of the International Searching Authority for PCT/US07/80983 dated Apr. 16, 2008, 9 pages.

PCT International Search Report and Written Opinion of the International Searching Authority for PCT/US07/80981, dated Apr. 16, 2008, 9 pages.

BIOPAC Systems, Inc., "Micro Pressure Measurement System—Product Overview," 39 pages.

"Fiber Optic Interferometer Fabry-Perot," available from http://physics.nad.ru/Physics/English/ifp_txt.htm at least as early as Oct. 15, 2007, 5 pages.

Medical Product Manufacturing News "Need to Know," 1 page, Sep. 2007.

BIOSEB: Samba—Blood Pressure System, available from http://www.bioseb.com/anglais/default/item_id=904_cat_id=3+Samba%20-%20Blood%20Pressure%System.php at least as early as Oct. 15, 2007, 4 pages.

Samba Sensors, "The Samba Technology," available from http://www.samba.se/index2.cfm?PageID=45 at least as early as Oct. 15, 2007, 1 page.

Samba Sensors, "Publications related to Samba Sensors AB," 3 pages.

Olaf J. Bick, et al., "The LETR-Principle: A Novel Method to Assess Electrode-Tissue Contact in Radiofrequency Ablation," Jul. 1998.

Masurement Specialties, Inc., "Piezo Film Sensors Technical Manual," Apr. 1999.

PCT International Search Report and Written Opinion of the International Searching Authority for PCT/US06/42119, dated Sep. 13, 2007, 9 pages.

* cited by examiner

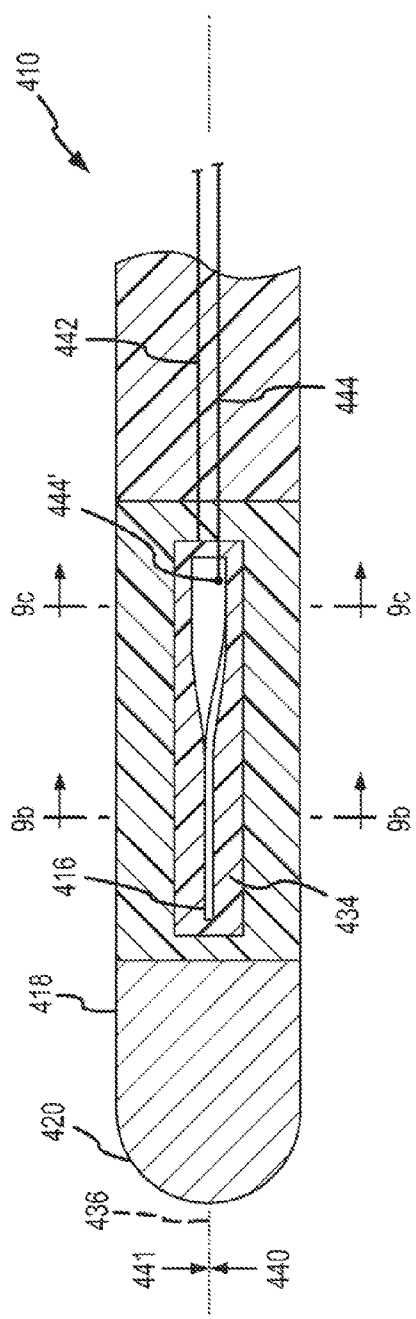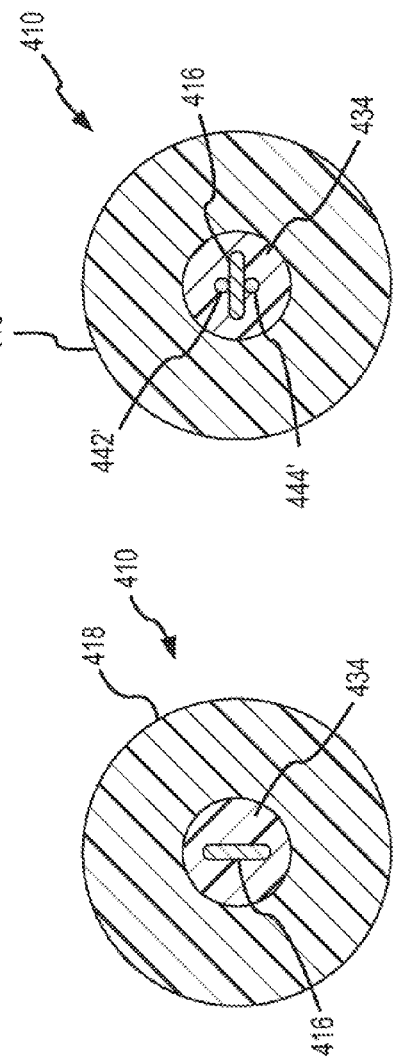

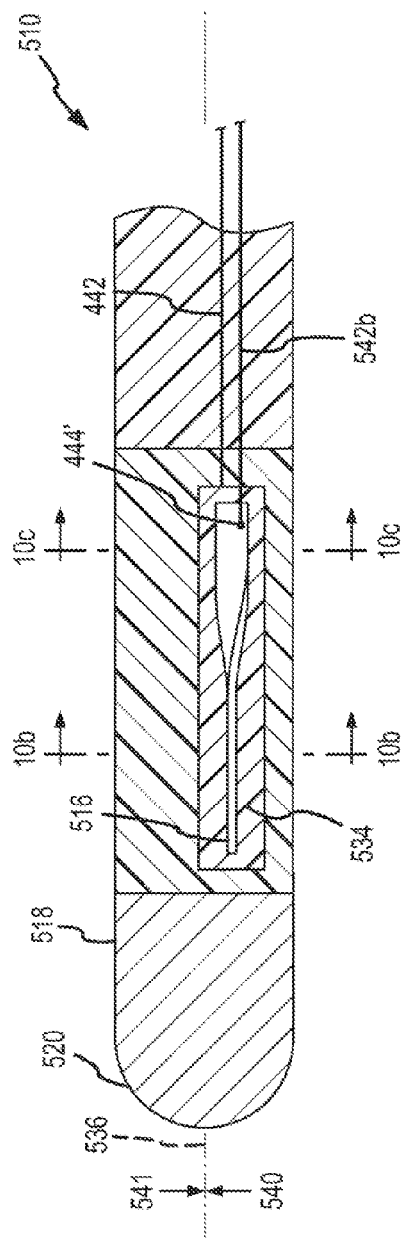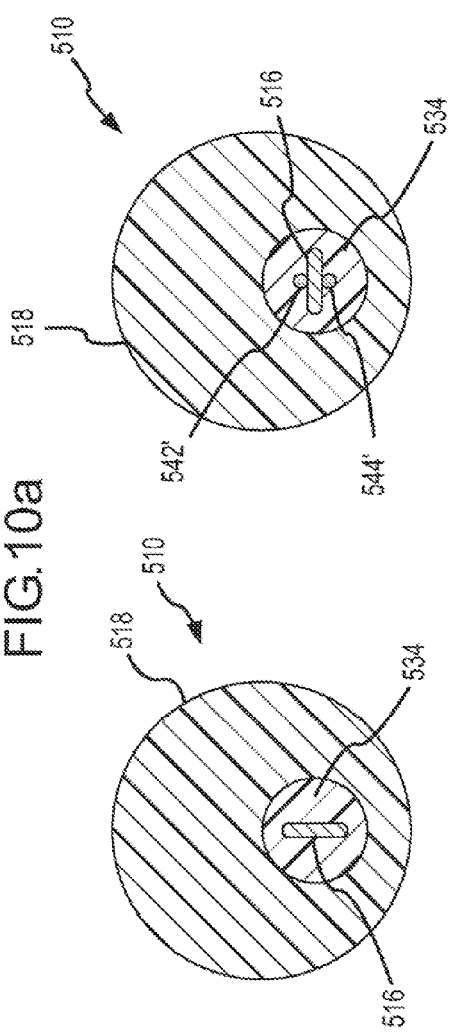
FIG.10a
FIG.10b
FIG.10c

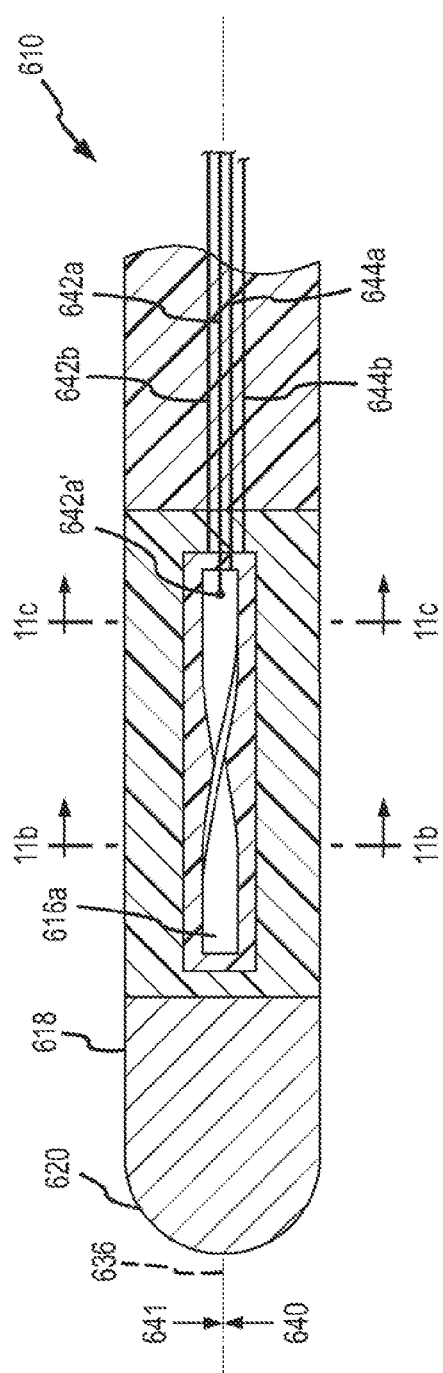
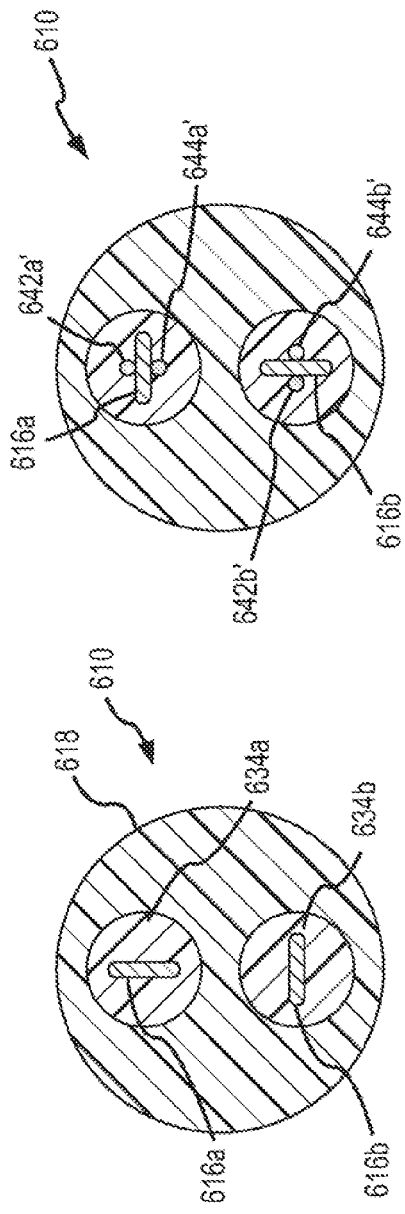
FIG.11a
FIG.11b
FIG.11c

DYNAMIC CONTACT ASSESSMENT FOR ELECTRODE CATHETERS

CROSS-REFERENCE TO RELATED APPLICATIONS

This application claims the benefit of U.S. provisional application Ser. No. 60/727,164, filed Oct. 13, 2005, which is hereby incorporated by reference as though fully set forth herein.

BACKGROUND OF THE INVENTION a. Field of the Invention

The instant invention is directed toward an electrode catheter and a method for using the electrode catheter for tissue ablation. In particular, the electrode catheter of the present invention may comprise one or more piezoelectric sensors for dynamically assessing catheter contact with a moving surface (e.g., the heart wall) for ablation procedures.

b. Background Art

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, lesions may be formed at specific locations in cardiac tissue via coagulation necrosis to lessen or eliminate undesirable atrial fibrillations.

Several difficulties may be encountered, however, when attempting to form lesions at specific locations using some existing ablation electrodes. One such difficulty encountered with existing ablation electrodes is how to assess tissue contact. Electrode-tissue contact is not readily determined using conventional fluoroscopy techniques. Instead, the physician determines electrode-tissue contact based on his/her experience using the electrode catheter. Such experience only comes with time, and may be quickly lost if the physician does not use the electrode catheter on a regular basis. In addition, when forming lesions in a heart, the beating of the heart further complicates matters, making it difficult to assess and maintain sufficient contact pressure between the electrode and the tissue for a sufficient length of time to form a desired lesion. If the contact between the catheter and the tissue cannot be properly maintained, a quality lesion is unlikely to be formed.

BRIEF SUMMARY OF THE INVENTION

It is desirable to be able to assess electrode contact with a moving surface (e.g., the heart wall) for tissue ablation procedures. When the electrode catheter is positioned against the heart wall, the beating of the heart deflects the electrode catheter. This deflection may be measured by implementing one or more piezoelectric sensor in the electrode catheter. The piezoelectric sensor(s) generates a voltage signal corresponding to movement or flexure of the electrode catheter.

In an exemplary embodiment, a piezoelectric sensor is oriented coaxially with the central axis of the electrode catheter. In another exemplary embodiment, a plurality of piezoelectric sensors are provided within the electrode catheter to assess catheter-tissue contact in endoluminal flow conditions. Output from the piezoelectric sensors enables a user (e.g., a physician or technician) to position the electrode catheter against a moving tissue with the desired amount of pressure for the ablation procedure.

An exemplary electrode catheter system for tissue ablation may comprise a flexible catheter shaft. At least one piezoelectric sensor oriented coaxial to the flexible catheter shaft, the at least one piezoelectric sensor responsive to movement of the flexible catheter shaft by generating electrical signals corresponding to the amount of movement. An output device is electrically connected to the at least one piezoelectric sensor, the output device receiving the electrical signals for dynamically assessing a level of contact between the flexible catheter shaft and a moving tissue.

In another exemplary embodiment, the system may be implemented for assessing the level of contact between the flexible catheter shaft and the moving tissue in endoluminal flow conditions.

An exemplary method of assessing catheter-tissue contact for tissue ablation may comprise: generating piezoelectric signals in response to movement of a flexible catheter, and dynamically assessing a level of contact between the flexible catheter and a moving tissue based on the piezoelectric signals.

The method may further comprise: generating simultaneous piezoelectric signals, comparing phase of the simultaneous piezoelectric signals, determining that the flexible catheter is free-floating in a hydrodynamic environment if the simultaneous piezoelectric signals are in-phase with each other, and determining that the flexible catheter is in contact with the moving tissue if the simultaneous piezoelectric signals are out-of-phase with each other, and vice versa.

The method may further comprise: generating simultaneous piezoelectric signals, comparing amplitude of the simultaneous piezoelectric signals, determining that the flexible catheter is free-floating in a hydrodynamic environment if the differences between the simultaneous piezoelectric signals are relatively attenuated, and determining that the flexible catheter is in contact with the moving tissue if the differences between the simultaneous piezoelectric signals are relatively elevated, and vice-versa.

Output may be conveyed to the user in real-time (e.g., at a display device or other interface) so that the user can properly position the electrode catheter on the target tissue with the desired level of contact for the ablation procedure. For example, the user may increase contact pressure if the output indicates insufficient contact. Or for example, the user may reduce contact pressure if the output indicates too much contact.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 2b is a cross-sectional view of the catheter taken along line 2b-2b in FIG. 2a.

FIG. 5b is a cross-sectional view of the catheter taken along lines 5b-5b in FIG. 5a.

FIG. 6b is a cross-sectional view of the catheter taken along lines 6b-6b in FIG. 6a.

FIG. 8b is a cross-sectional view of the catheter taken along lines 8b-8b in FIG. 8a.

FIG. 9a is a cross-sectional view of a portion of another exemplary catheter with a piezoelectric sensor. FIG. 9b is a cross-sectional view of the catheter taken along lines 9b-9b in FIG. 9a. FIG. 9c is a cross-sectional view of the catheter taken along lines 9c-9c in FIG. 9a.

FIG. 10a is a cross-sectional view of a portion of another exemplary catheter with a piezoelectric sensor. FIG. 10b is a cross-sectional view of the catheter taken along lines 10b-10b in FIG. 10a. FIG. 10c is a cross-sectional view of the catheter taken along lines 10c-10c in FIG. 10a.

FIG. 11a is a cross-sectional view of a portion of another exemplary catheter with a piezoelectric sensor. FIG. 11b is a cross-sectional view of the catheter taken along lines 11b-11b in FIG. 11a. FIG. 11c is a cross-sectional view of the catheter taken along lines 11c-11c in FIG. 11a.

DETAILED DESCRIPTION OF THE INVENTION

Exemplary embodiments of a tissue ablation system and methods of use to assess dynamic contact between an electrode catheter and a moving tissue are depicted in the figures. Exemplary systems comprise an electrode catheter which may be inserted into the patient e.g., for forming ablative lesions inside the patient's heart. During an exemplary ablation procedure, a user (e.g., the patient's physician or a technician) may insert the catheter into one of the patient's blood vessels, e.g., through the leg or the patient's neck. The user, guided by a real-time fluoroscopy imaging device, moves the catheter into the patient's heart.

When the catheter reaches the patient's heart, electrodes at the distal portion of the catheter may be implemented to electrically map the myocardium (i.e., muscular tissue in the heart wall) and locate a target tissue. After locating the target tissue, the user must move the catheter into contact with the target tissue before applying ablative energy to form an ablative lesion or lesions. The level of contact is often critical to form sufficiently deep ablative lesions on the target tissue without damaging surrounding tissue in the heart.

As described further below, the catheter may comprise one or more piezoelectric sensors which generate electric signals in response to the catheter coming into contact with a moving surface (e.g., target tissue within the beating heart). Accordingly, embodiments of the present invention provide a number of advantages, including, for example, the ability to apply a reasonable amount of ablative energy to a target tissue while mitigating tissue contact problems. The invention also facilitates enhanced tissue contact in difficult environments (e.g., during lesion formation on a moving surface inside a beating heart).

Figure 1A:
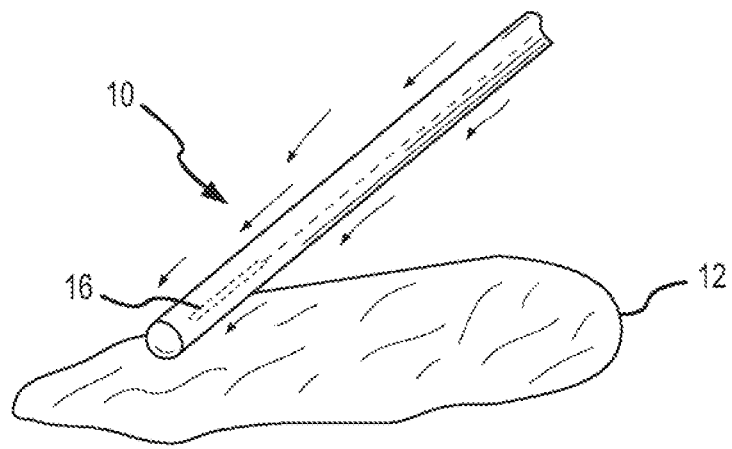
FIGS. 1a and 1b illustrate exemplary contact between an electrode catheter and a moving target tissue.
Figure 1B:
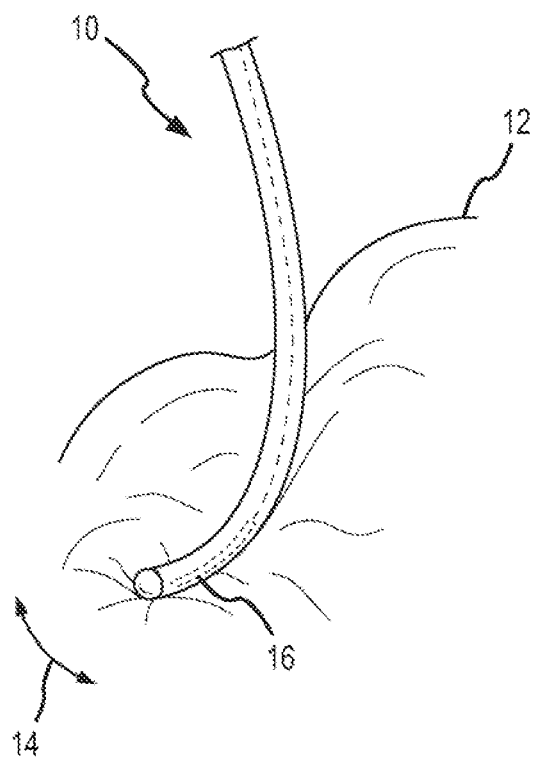

FIGS. 1a and 1b illustrate exemplary contact between an electrode catheter 10 and a moving target tissue 12 (e.g., myocardium). In FIG. 1a, the catheter 10 is shown having little, if any, contact with the target tissue 12, e.g., as the catheter 10 may be "floating" adjacent the target tissue 12 as the user is positioning the catheter 10 in the heart for an ablation procedure. In FIG. 1b, the catheter 10 is shown in contact with the target tissue 12.

When the catheter 10 is in sufficient or "good" contact with the target tissue 12, the catheter 10 may move or be deflected by movement of the target tissue 12 generally in the directions illustrated by arrows 14. Movement of the catheter 10 may be measured in real-time to assess contact between the catheter 10 and the moving target tissue 12, as described more fully below.

Before continuing, it is noted that the contact and motion illustrated by FIG. 1b is shown for purposes of illustration and is not intended to be limiting. Other contact and motion may also exist and/or be desired by the user. The definition of sufficient or "good" contact may depend at least to some extent on various operating conditions, such as, e.g., the type of target tissue, desired depth of the ablation lesion, and power and duration of the applied RF energy, to name only a few examples.

It is also noted that other components typical of systems which are conventionally implemented for tissue ablation are not shown or described herein for purposes of brevity. Such components may nevertheless also be provided as part of, or for use with, the catheter 10. For example, these systems commonly include or are used in conjunction with an ECG recording system, and/or various controls for performing the ablation procedure. Such components are well understood in the medical devices arts and therefore further explanation is not necessary for a complete understanding of the invention.

As mentioned above, the catheter 10 may comprise one or more piezoelectric sensors 16 to measure movement or deflection of the catheter 10 when in contact within the moving target tissue 12. Piezoelectric sensors respond to mechanical movement by generating electrical energy (e.g., a voltage). Accordingly, when the catheter 10 is positioned in contact with the moving target tissue 12, piezoelectric sensor(s) 16 generate an electrical signal corresponding to movement or deflection of the catheter 10. The resulting electrical signal may be processed and/or otherwise output for the user so that the user is able to determine when the catheter 10 is positioned with the desired level of contact with the moving target tissue 12.

Figure 2A:
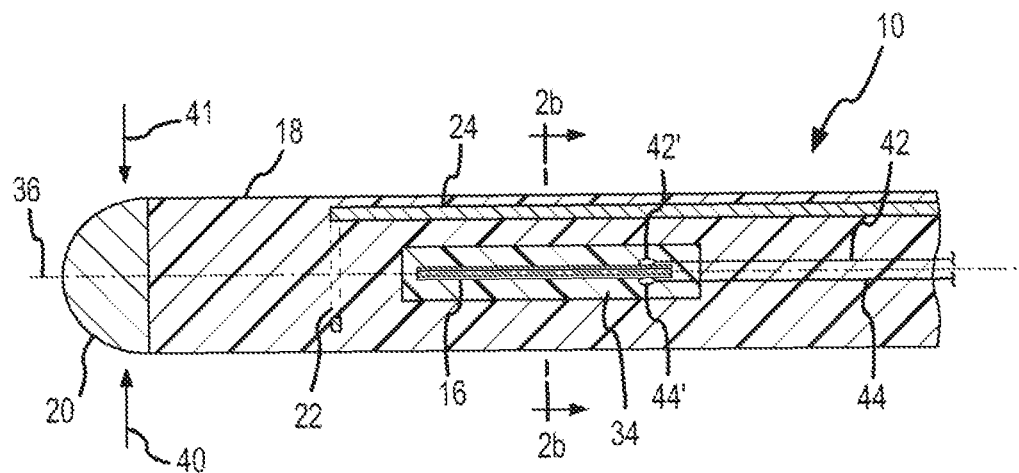
FIG. 2a is a cross-sectional view of a portion of an exemplary catheter with a piezoelectric sensor.
Figure 2B:
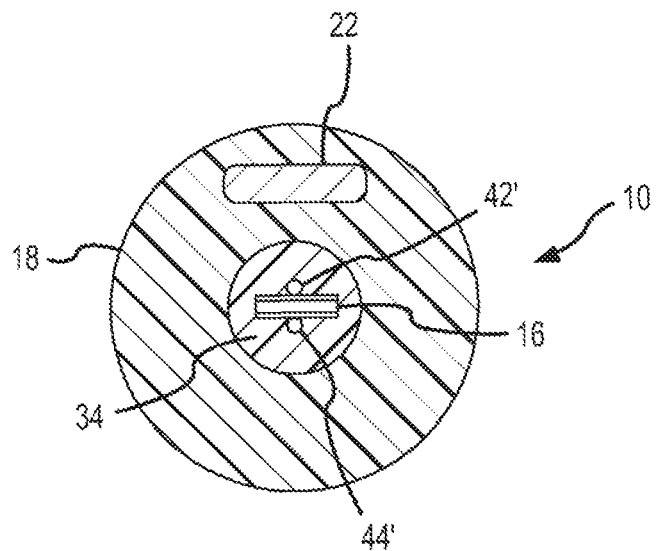

FIG. 2a is a cross-sectional view of a portion of an exemplary catheter 10 with a piezoelectric sensor 16. FIG. 2b is a cross-sectional view of the catheter 10 taken along line 2b-2b in FIG. 2a. The portion of catheter 10 shown in FIGS. 2a and 2b is the portion which may be inserted into the patient's heart for an ablation procedure (e.g., the portion of catheter 10 shown in FIGS. 1a and 1b).

Catheter 10 may comprise a flexible catheter shaft 18. The flexible catheter shaft 18 may be made of a plastic or other suitable material which enables the catheter 10 to be readily inserted into the patient's heart through the blood vessels, and to be moved or deflected by movement of an adjacent tissue (e.g., target tissue 12 shown in FIGS. 1a and 1b).

An electrode 20 may be provided at a distal portion of the catheter shaft 18. The electrode 20 may be electrically connected via suitable wiring through the catheter shaft 18 to a generator (not shown), such as, e.g., a radio frequency (RF) generator. The electrode 20 is thus operable to emit electrical energy (e.g. RF radiation) near the tip of the catheter 10 for forming ablation lesion(s) on the target tissue during ablation procedures.

A pull ring 22 may be provided in the flexible catheter shaft 18 of the catheter 10. Pull ring 22 may be operatively associated with a pull wire 24 extending through the flexible catheter shaft 18 to a handle portion (not shown) outside of the patient's body. Accordingly, the handle portion may be grasped and operated by the user for manually positioning the catheter shaft 18 inside the patient's heart so that the electrode 20 is in contact with the target tissue, e.g., as illustrated in FIG. 1b.

As mentioned above, catheter 10 may also comprise at least one piezoelectric sensor 16 which may be implemented to assess a level of contact between the electrode 20 and the target tissue for the ablation procedure. Piezoelectric sensors which generate electrical energy in response to applied mechanical stress are well-understood in the electro-mechanical arts.

In general, piezoelectric sensors comprise a piezoelectric material which contains positive and negative electrical charges. In a neutral or "non-stressed" state, these electrical charges are symmetrically distributed in the piezoelectric material such that the material exhibits an overall neutral electrical charge. However, subjecting the piezoelectric material to a mechanical stress (e.g., flexure, pressure, and/or tension) disturbs the symmetrical distribution of electrical charges, thereby generating electrical energy across the material. Even minor deformation of some piezoelectric materials (e.g., on the order of nanometers) may generate a measurable voltage signal.

Figure 3A:
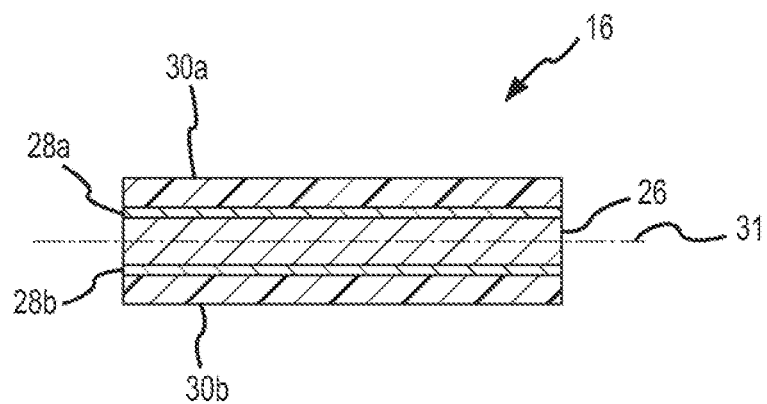
FIG. 3a is a cross-sectional view of an exemplary piezoelectric sensor which may be implemented for use with the catheter.

FIG. 3a is a cross-sectional view of an exemplary piezoelectric sensor 16 which may be implemented for use with the catheter 10. In an exemplary embodiment, the piezoelectric sensor 16 may be a laminated sensor, having a plurality of laminated layers. Laminating the sensor increases its sensitivity.

The laminated layers may comprise a piezoelectric material 26 "sandwiched" between metal layers 28a and 28b and protective coating 30a and 30b. Metal layers 28a and 28b may be any suitable metal, e.g., a thin layer of silver ink. The metal layers 28a and 28b serve to collect electrical charge generated by the piezoelectric material 260 e.g. for delivery as electrical signals via electrical wiring to a data acquisition/processing/output device. Providing metal layers 28a and 28b serve to collect symmetric electrical energy in response to equi-amplitude deflections of the piezoelectric material 26 in either direction, and therefore is particularly desirable for use with bi-directionally deflectable catheters. Protective coating 30a and 30b may be any suitable material, e.g. Mylar®.

It is noted that the laminated layers are not limited to any particular material and/or configuration. For example, the piezoelectric sensor 16 is not limited to use with separate metal layers 28a and 28b. Nor is the piezoelectric sensor 16 limited to the generally rectangular configuration shown in FIG. 3a.

In an exemplary embodiment, the piezoelectric material 26 may comprise a thin, flexible, polymer-based material. One such piezoelectric film is a polyvinylidene fluoride (PVDF) film commercially available from the Sensor Products Division of Measurement Specialties, Inc. (Norristown, Pa.). This PVDF film is approximately 28 μm thick, enabling the PVDF film to be readily housed within the catheter shaft 18 (see FIGS. 2a and 2b).

In addition, this PVDF film has a wide frequency range of about 0.001 Hz to $10^9$ Hz and a high dynamic stress constant ($g_{31}$=216×$10^{-3}$ Vm/N). For purposes of illustration, other common piezoelectric materials, such as lead zirconate titanate (PZT) has a dynamic stress constant ($g_{31}$) of 10×$10^{-3}$ Vm/N, and barium titanium oxide ($BaTiO_3$) has a dynamic stress constant ($g_{31}$) of 5×$10^{-3}$ Vm/N. Accordingly, the PVDF film is very sensitive, exhibiting a relatively high voltage response to relatively small mechanical stresses, and is therefore well-suited for measuring dynamic stresses and strains that a moving tissue may exert on the catheter shaft 18.

Of course the piezoelectric sensor 16 described above with reference to FIG. 3a is for purposes of illustration and not intended to be limiting. Other piezoelectric sensors may also be implemented, and are not limited to laminated piezoelectric film. Nor are piezoelectric sensors limited to use with any particular type or size of piezoelectric material. Selection of piezoelectric sensor 16 for use with the catheter 10 may be application-specific and depend at least in part on one or more design considerations, such as, but not limited to, the desired sensitivity and/or spatial constraints for housing the piezoelectric sensor.

Piezoelectric sensor 16 is shown in FIG. 3a in a neutral state. In the neutral state, the piezoelectric material 26 is not subject to any stresses or strains. Accordingly, the electrical charges are symmetrically distributed on either side of the neutral plane 31 in the piezoelectric material 26 such that the material exhibits an overall neutral electrical charge.

Figure 3B:
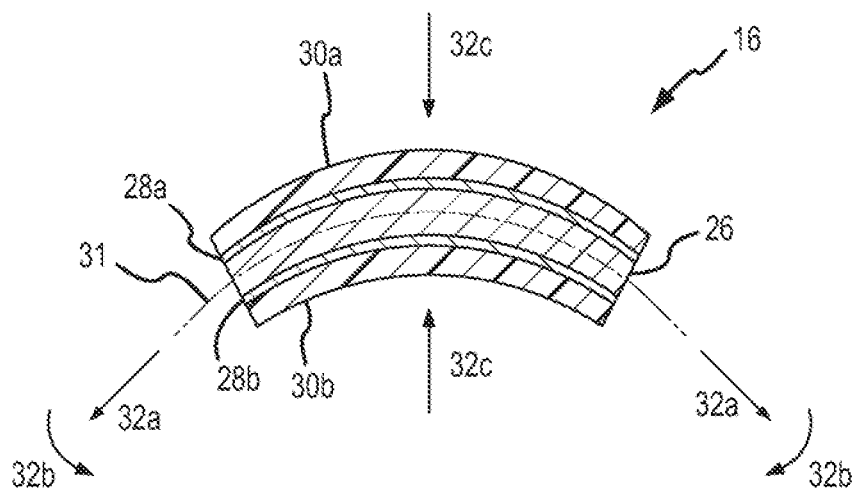
In FIG. 3b, the piezoelectric sensor is shown in exaggerated form as it may respond to a stress applied generally in the direction of arrow.

In FIG. 3b, the piezoelectric sensor 16 is shown in exaggerated form as it may respond to longitudinal stresses applied generally in the direction of arrows 32a. In this stressed state, the piezoelectric material 26 longitudinal strain relative to its neutral state. Accordingly, the symmetrical distribution of electrical charges is disturbed, and electrical energy is generated across the piezoelectric material 26. This electrical energy may be collected by metal layers 28a, 28b, e.g., for delivery as an electrical signal via electrical wiring in the catheter 10 to a data acquisition/processing/output device (not shown).

It is noted that the piezoelectric sensor 16 may also respond to bending stresses applied generally in the direction of arrows 32b. In this stressed state, the piezoelectric material 26 undergoes flexural strain relative to its neutral state. Accordingly, the symmetrical distribution of electrical charges is disturbed, and electrical energy is generated across the piezoelectric material 26. This electrical energy may be collected by metal layers 28a, 28b, e.g., for delivery as an electrical signal via electrical wiring in the catheter 10 to a data acquisition/processing/output device (not shown).

Furthermore, the piezoelectric sensor 16 may also respond to transverse stresses applied generally in the direction of arrows 32c. In this stressed state, the piezoelectric material 26 undergoes transverse strain relative to its neutral state. Accordingly, the symmetrical distribution of electrical charges is disturbed, and electrical energy is generated across the piezoelectric material 26. This electrical energy may be collected by metal layers 28a, 28b, e.g., for delivery as an electrical signal via electrical wiring in the catheter 10 to a data acquisition/processing/output divide (now shown).

Turning again to FIGS. 2a and 2b, piezoelectric sensor 16 is shown housed within the catheter shaft 18. For example, piezoelectric sensor 16 may be provided within an insulated cavity or compliant section 34 formed within the catheter shaft 18. In addition to housing the piezoelectric sensor 16 in the catheter 10, and protecting the piezoelectric sensor 16 from external damage or corrosion, the compliant section 34 serves as a low pass mechanical filter. That is, the compliant section 34 attenuates high frequency "noise" signals caused, e.g., by minor vibrations from intermittent contact during positioning of the catheter 10 adjacent the target tissue. Accordingly, high frequency noise signals are damped, or even non-existent, as output for the user.

The piezoelectric sensor 16 may be oriented within the catheter shaft 18 to provide the desired sensitivity. By way of example, piezoelectric sensor 16 is shown in FIGS. 2a and 2b centrally oriented in the catheter shaft 18, with the plane 31 (see FIG. 3a) of the piezoelectric sensor 16 substantially parallel to the central axis or neutral plane 36 of the catheter shaft 18. Accordingly, the piezoelectric sensor 16 is responsive to movement or deflection of the catheter shaft 18 relative to the neutral plane 36, e.g., in the directions illustrated by arrows 40 and 41.

Other embodiments are also contemplated as being within the scope of the invention. By way of example, the piezoelectric sensor 16 is not limited to being centrally oriented in the catheter shaft 18. Piezoelectric sensor 16 may be offset from the central axis or neutral plane 36, as further discussed below with reference to FIGS. 5a and 5b. Also by way of example, the piezoelectric sensor 16 is not limited to being housed within the catheter shaft 18. Piezoelectric sensor 16 may be laminated to an outer surface of the catheter shaft 18, as further discussed below with reference to FIGS. 6a and 6b. Still other configurations are also contemplated.

Electrical wiring 42 and 44 may be connected to the piezoelectric sensor 16 (e.g., as illustrated by connections 42' and 44') and extend through the catheter shaft 18 to deliver electrical signals from the piezoelectric sensor 16 to a data acquisition/processing/output device (not shown), such as e.g., an echocardiogram (ECG) device. Alternatively, a wireless connection may be implemented, e.g., by providing a transmitter in the catheter and a receiver in association with the data acquisition/processing/output device.

Figure 4:
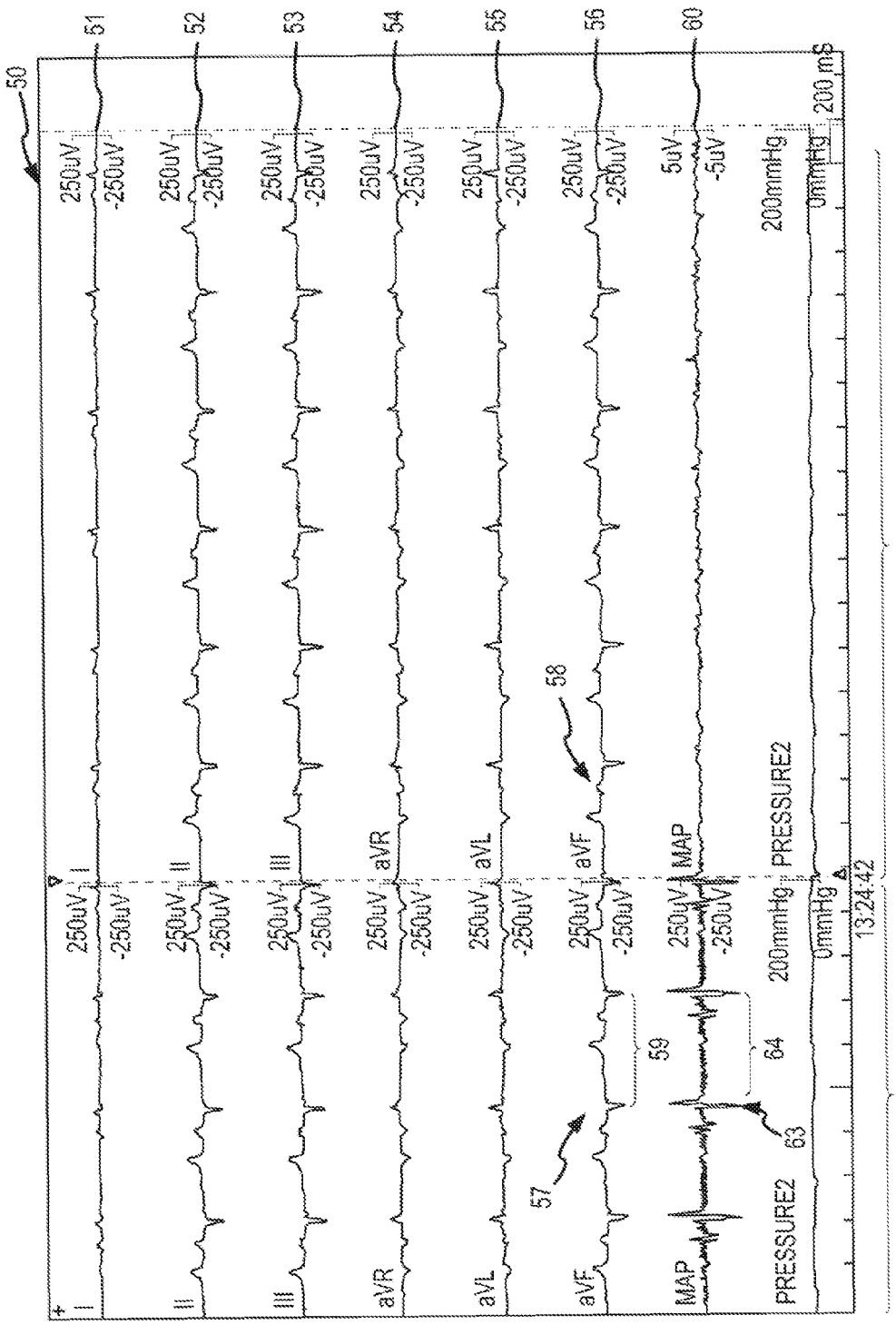
FIG. 4 shows exemplary output of an ECG device showing waveforms corresponding to a patient's heartbeat, and a waveform corresponding to electrical signals generated by a piezoelectric sensor in a catheter inserted into the patient's heart.

During operation, piezoelectric sensor 16 generates electrical (voltage) signals in response to movement or deflection of the catheter shaft 18 (e.g., in the directions illustrated by arrows 40 and 41 in FIG. 2a). These electrical signals may be viewed by the user, e.g., as output on an ECG device. FIG. 4 shows exemplary output 50 of an ECG device showing waveforms 51-56 corresponding to a patient's heartbeat, and a waveform 60 corresponding to electrical signals generated by a piezoelectric sensor 16 in a catheter 10 inserted into the patient's heart.

It is well-understood in the medical sciences that heart wall motion (or heartbeat) is due to electrical signals in the heart that cause myocardial contractions. The heart wall motion may be detected and displayed for a user on an ECG device, e.g., as waveforms 51-56. By way of example, peaks 57 and 58 in waveform 56 correspond to heartbeats. The period (time between heartbeats) is also observed, e.g., as period 59.

Similarly, output from the piezoelectric sensor 16 may be displayed on the ECG device, e.g., as waveform 60. Accordingly, the output may be implemented to assess dynamic contact between a catheter 10 and a moving tissue. In the example shown in FIG. 4, a catheter was positioned in good contact with a moving heart wall being monitored by waveforms 51-56 during time 61, and the catheter was removed from contact with the moving heart wall during time 62.

In an exemplary embodiment, the signal strength (e.g., amplitude) from the piezoelectric sensor is proportional to the amount of movement or deflection of the catheter, and therefore can be used to determine if the catheter is in good contact with a moving tissue (e.g., the myocardium). For example, the signal strength (as observed by the peaks in waveform 60) is strong during time 61 when the catheter was in good contact with the moving heart wall, and the signal strength is weak when the catheter was removed from contact with the moving heart wall during time 62. Accordingly, the signal strength may indicate a level of contact between the catheter and moving tissue.

In addition, the output (waveform 60) may be used for dynamic contact assessment. That is, electrical signals are generated by the piezoelectric sensor in response to movement of the catheter shaft. If the catheter shaft is not in contact with the moving target tissue, or is in contact with a stationary tissue, there are no peaks in the resulting waveform 60 (or the peaks are intermittent). On the other hand, a strong correlation between the heartbeat (e.g., peak 57) and output by the piezoelectric sensor (e.g., peak 63) indicates that the catheter shaft is in good contact with the moving target tissue.

Signal periodicity is also a strong indicator of dynamic contact assessment. For example, the period 59 between heartbeats corresponds well with the period 64 between output by the piezoelectric sensor, indicating that the catheter is moving in response to the heartbeat (and not some other reason).

It is observed in FIG. 4 that output from the piezoelectric sensor (waveform 60) corresponds with both the peaks and the periodicity of the patient's heartbeat (waveforms 51-56). Therefore, the user is able to use this output for assessing the level of contact between the catheter and the moving heart wall, e.g., for an ablation procedure. The user may also assess the level of contact between the catheter 10 and the moving heart wall. In an exemplary embodiment, higher amplitude output (e.g., in waveform 60) indicates more contact, and lower amplitude indicates less contact. The user can use this feedback to increase or decrease contact of the catheter with the moving heart wall to achieve the desired contact.

Before continuing, it is noted that although the waveforms shown in FIG. 4 are output on an ECG device such as may be used for monitoring a patient's heartbeat, the present invention is not limited to use with any particular type of output device. Any suitable analog and/or digital device may be implemented for indicating electrode-tissue contact to a user. In another exemplary embodiment, the electrical signals generated by piezoelectric sensor 16 may be further characterized using a suitable processing device such as, but not limited to, a desktop or laptop computer. Such processing device may be implemented to receive the voltage signal generated by the piezoelectric sensor and convert it to a corresponding contact condition for the catheter 10 and output for the user, e.g., at a display device.

Of course the output device is not limited to a displays device. For example, the electrode-tissue contact may be output to the user as an audio signal or tactile feedback (e.g.,) vibrations) on the handle of the catheter. In any event, circuitry for conveying output of the piezoelectric sensor to a user in one form or another may be readily provided by those having ordinary skill in the electronics arts after becoming familiar with the teachings herein.

Figure 5A:
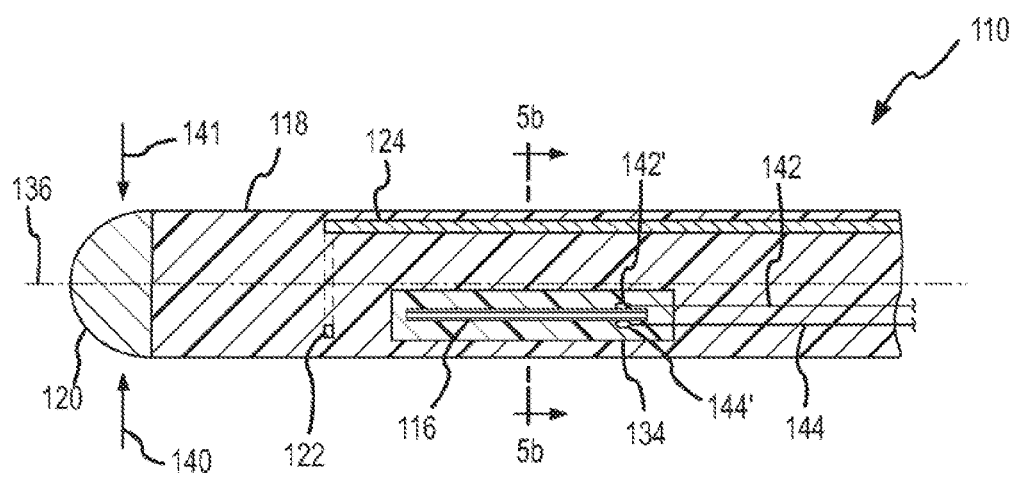
FIG. 5a is a cross-sectional view of a portion of another exemplary catheter with a piezoelectric sensor.
Figure 5B:
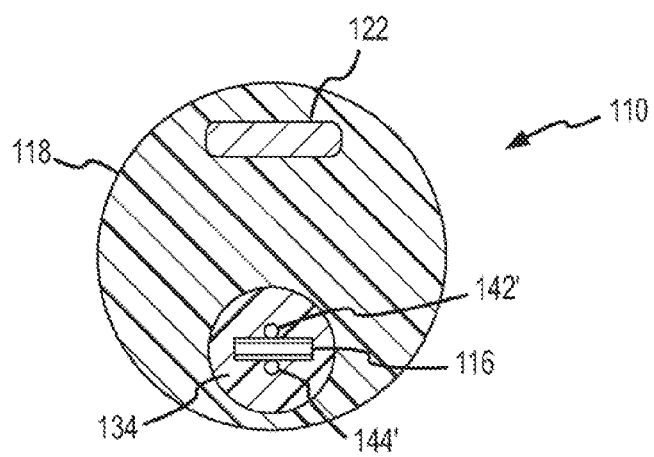

FIG. 5a is a cross-sectional view of a portion of another exemplary catheter 110 with a piezoelectric sensor 116. FIG. 5b is a cross-sectional view of the catheter 110 taken along lines 5b-5b in FIG. 5a. It is noted that 100-series reference numbers are used in FIGS. 5a and 5b to refer to like elements described above with reference to FIGS. 2a and 2b. Therefore the description of some elements may not be repeated in the discussion of FIGS. 5a and 5b.

Catheter 110 may comprise a flexible catheter shaft 118 with at least one piezoelectric sensor 116. The piezoelectric sensor 116 is oriented such that the plane 31 (FIG. 3a) is substantially parallel to the central axis or neutral plane 136 of the catheter shaft 118 such that the sensor 116 is responsive to movement or deflection in the direction of arrow 140 and/or arrow 141. In this example, however, the piezoelectric sensor 116 is positioned off-center, or eccentrically away from the central axis 136 of the catheter shaft 118.

Such an embodiment may be implemented with irrigated catheters. Irrigated catheters typically include one or more fluid tubes (not shown) for delivering medication or other fluids to the tissue. These fluid tubes may extend through the catheter 110 along or in the general direction of its central axis, e.g., to protect the fluid tubes from damage and resulting potentially harmful release of the fluid elsewhere in the patient's body. Therefore, positioning the piezoelectric sensor 116 in the catheter shaft 118 substantially as shown in FIGS. 5a and 5b enables the use of piezoelectric sensor 116 with conventionally available irrigated catheters.

Such an embodiment may also be implemented to provide greater sensitivity to movement of the catheter shaft 118 (e.g., in the direction illustrated by arrow 140). That is, positioning the piezoelectric sensor 116 off-center and closer to the outer diameter of the catheter 110 enables the piezoelectric sensor 116 to detect lesser stresses on the catheter shaft 118 than if the piezoelectric sensor 116 is positioned along the central axis 136 of the catheter shaft. Indeed, the stress on piezoelectric sensor 116 increases the closer the piezoelectric sensor 116 is positioned to the outer diameter. In response, the piezoelectric sensor 116 generates stronger (higher amplitude) signals.

Figure 6A:
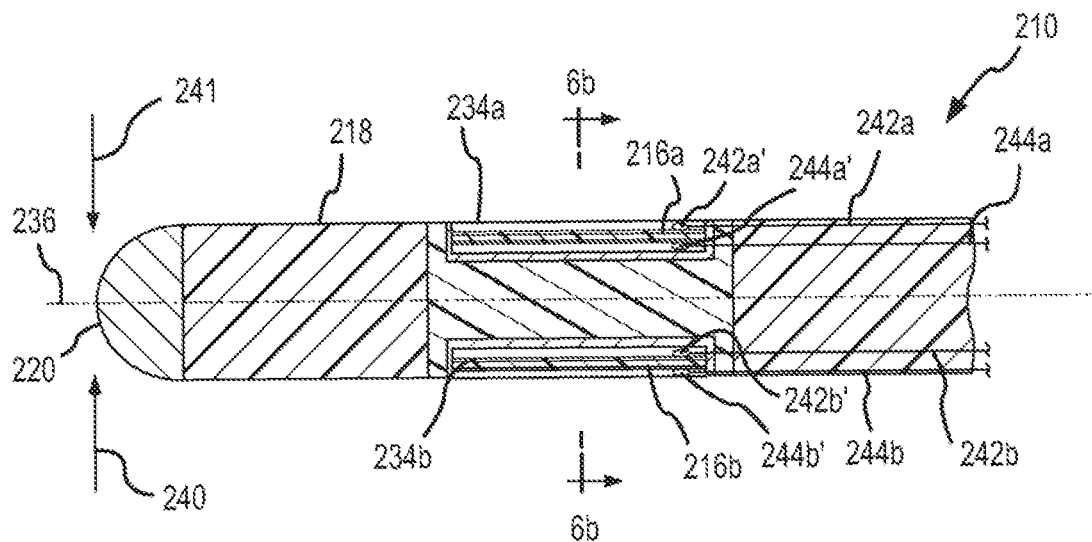
FIG. 6a is a cross-sectional view of a portion of another exemplary catheter with a plurality of piezoelectric sensors.
Figure 6B:
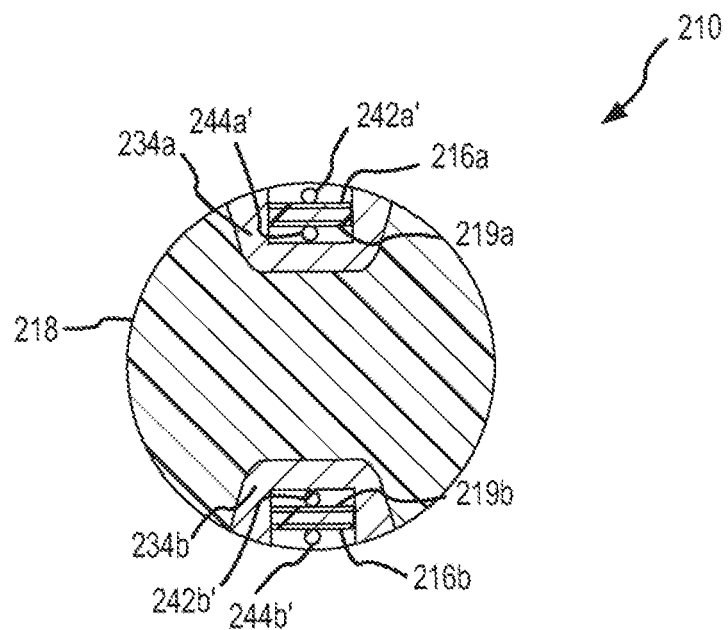

FIG. 6a is a cross-sectional view of a portion of another exemplary catheter 210 with a plurality of piezoelectric sensors 216. FIG. 6b is a cross-sectional view of the catheter 210 taken along lines 6b-6b in FIG. 6a. It is noted that 200-series reference numbers are used in FIGS. 6a and 6b to refer to like elements described above with reference to FIGS. 2a and 2b. Therefore the description of some elements may not be repeated in the discussion of FIGS. 6a and 6b. In addition, the pull ring and pull cord is omitted from FIGS. 6a and 6b to simplify the drawings.

Catheter 210 may comprise a flexible catheter shaft 218 with a plurality of piezoelectric sensors 216a and 216b. Although two piezoelectric sensors 216a and 216b are shown, it is noted that two or more sensors may be implemented for this embodiment. The piezoelectric sensors 216a and 216b are oriented such that the plane 31 is substantially parallel to the central axis or neutral plane 236 of the catheter shaft 218 such that the sensors 216a and 216b are responsive to movement or deflection in the direction of arrow 240 and or arrow 241.

In this example, however, the piezoelectric sensors 216a and 216b are provided on the outer surface of the catheter shaft 218. For example, each of the piezoelectric sensors 216a, 216b in may comprise a piezoelectric film applied to the surface of the catheter shaft 218 and insulated by a compliant layer 234a and 234b, respectively. Of course, other embodiments are also contemplated wherein the piezoelectric sensors 216a and 216b are provided within the catheter shalt 218.

In an exemplary embodiment, piezoelectric sensors 216a and 216b may be positioned on diametrically opposite surfaces of catheter shaft 218, such that the sensor poles 219a and 219b (FIG. 6b) face each other (i.e., the inner surface of catheter shaft 218). Each of the sensors 216a, 216b has the same electrical polarity, and the sensor poles 219a and 219b are connected together to the same reference potential (e.g., ground).

The embodiment shown in FIGS. 6a and 6b may be implemented for assessing contact with a moving tissue in endoluminal flow applications, e.g., when the catheter 210 is surrounded by blood flowing through the heart while positioning the catheter 210 against the heart wall. Output from the piezoelectric sensors 216a and 216b indicates if the catheter 210 is free-floating in a hydrodynamic environment (e.g., surrounded by blood flow as shown in FIG. 1a), or if the catheter 210 is positioned in contact with the moving tissue (e.g., as shown in FIG. 1b).

Figure 7A:
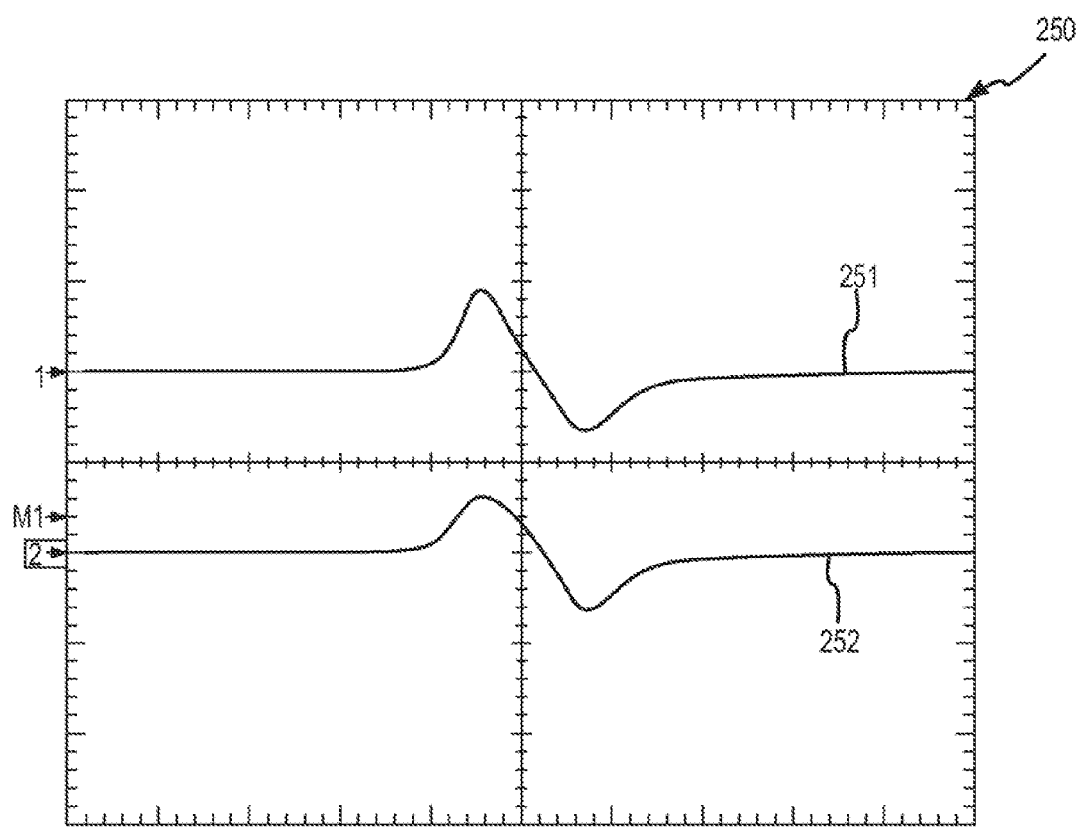
FIG. 7a shows exemplary output of an ECG device showing waveforms corresponding to electrical signals generated by two piezoelectric sensors in the catheter discussed above with reference to FIGS. 6a and 6b.
Figure 7B:
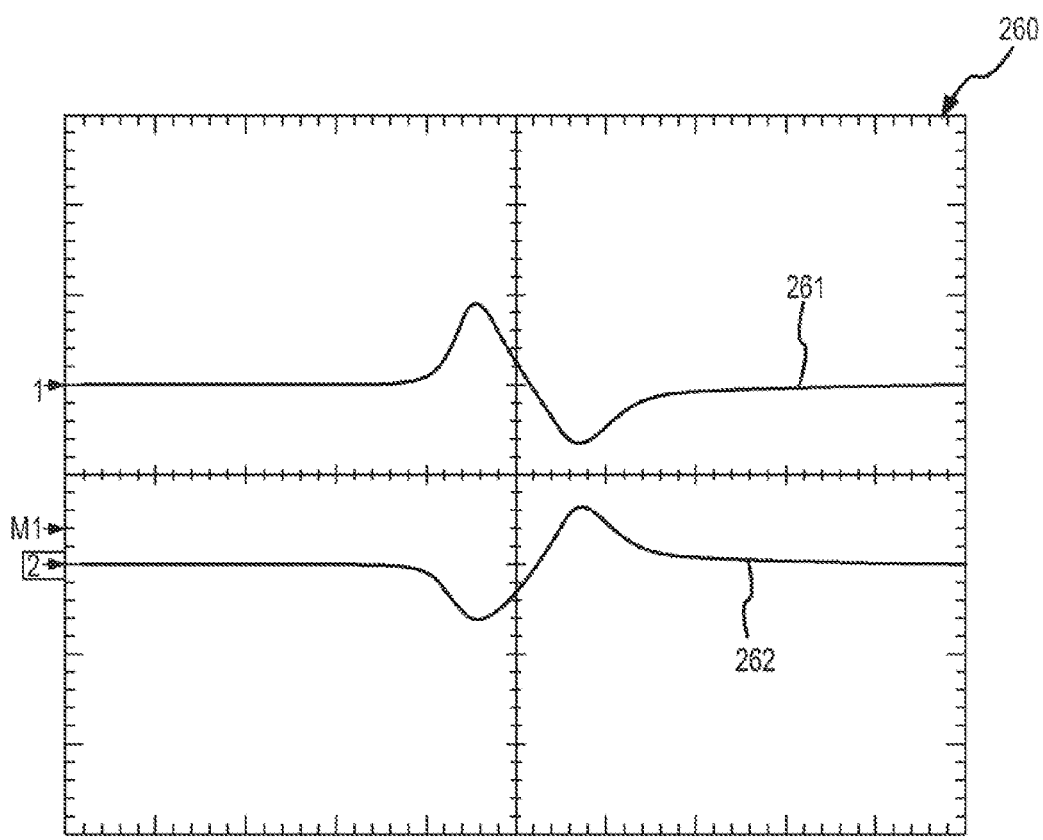
FIG. 7b shows exemplary output of an ECG device showing waveforms corresponding to electrical signals generated by two piezoelectric sensors in the catheter discussed above with reference to FIGS. 6a and 6b.
Figure 7C:
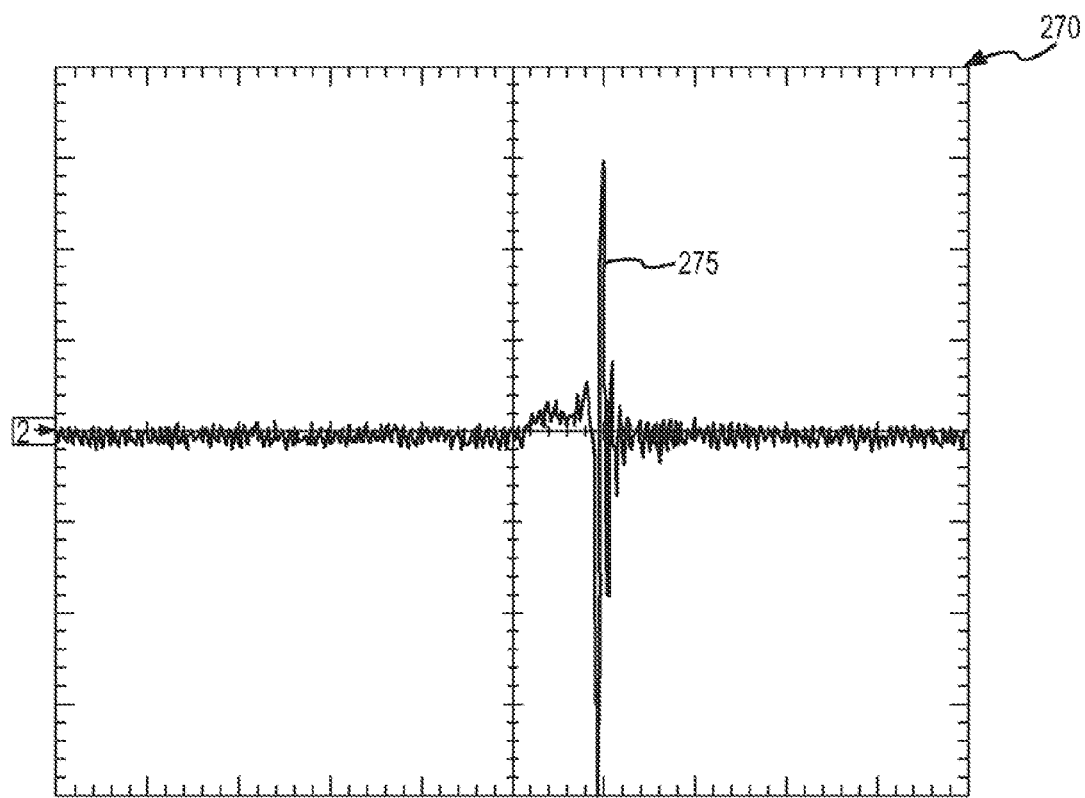
FIG. 7c shows exemplary output of an ECG device showing waveform corresponding to the combined output of both piezoelectric sensors as shown in FIG. 7b.

Such an implementation may be better understood with reference to the exemplary output from piezoelectric sensors 216a and 216b as shown in FIGS. 7a, 7b, and 7c. FIG. 7a shows exemplary output 250 of an ECG device showing waveforms 251 and 252 corresponding to electrical signals generated by two piezoelectric sensors in the catheter 210 is discussed above with reference to FIG. 6a and 6b. In this example, the catheter 210 is in a hydrodynamic environment (i.e., it is surrounded by blood flowing, through the heart).

Hydrodynamic pressure fluctuations are isotropic in nature. When the catheter 210 is being positioned within the patient's heart the blood flow through the heart around the catheter 210 exerts approximately the same pressure on the catheter 210 in all directions. Accordingly, the output from each of the piezoelectric sensors 216a and 216b is approximately the same (i.e., the waveforms are "in-phase" with one another). Such output indicates that the catheter 210 is free-floating and not in contact with the moving tissue.

It is observed that when the catheter 210 is free-floating, the output of each sensor 216a, 216b is almost the same, and the waveforms 251 and 252 are approximately in-phase with one another. Under ideal conditions, these waveforms 251 and 252 can be combined to have a canceling or additive effect when combined. Of course a patient's heart may not provide such ideal conditions. However, the waveforms 251 and 252 should approximately cancel one another, thereby indicating that the catheter 210 is in an endoluminal flow environment.

FIG. 7b shows exemplary output 260 of an ECG device showing waveforms 261 and 262 corresponding to electrical signals generated by two piezoelectric sensors in the catheter 210 discussed above with reference to FIGS. 6a and 6b. In this example, the catheter 210 is positioned against a moving heart wall.

When the catheter 210 is in contact with the moving tissue, one of the piezoelectric sensors (e.g., sensor 216a) contracts in response to the movement of the tissue and the other sensor (e.g. sensor 216b) is extended. Accordingly, the output from the piezoelectric sensors 216a and 216b is approximately opposite one an other (i.e., the waveforms are "out-of-phase" with one another). Such output indicates that the catheter 210 is in contact with the moving tissue.

It is observed that when the catheter 210 is positioned against a moving tissue, the sensors 216a and 216b are subject to opposite stresses, and the waveforms 261 and 262 are approximately out-of-phase with one another. Under ideal conditions, combining the two waveforms 261 and 262 has a cancelling or additive effect. Of course a patient's heart may not provide such ideal conditions. However, the waveforms 261 and 262 should approximately double the output, thereby indicating that the catheter 210 is in contact with the moving heart wall.

FIG. 7c shows exemplary output 270 of an ECG device showing waveform 275 corresponding to the combined output of both piezoelectric sensors as shown in FIG. 7b. It is observed that the output is approximately double the individual output and is due to the additive effect.

Figure 8A:
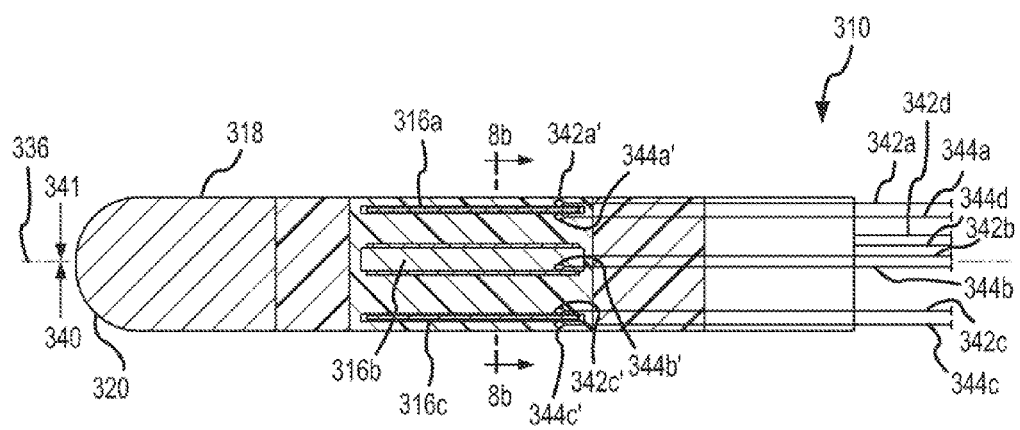
FIG. 8a is a cross-sectional view of a portion of another exemplary catheter with a piezoelectric sensor.
Figure 8B:
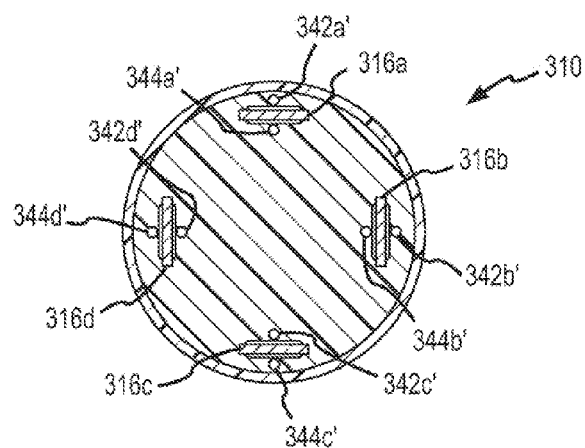

FIG. 8a is a cross-sectional view of a portion of another exemplary catheter 310 with a piezoelectric sensor 316. FIG. 8b is a cross-sectional view of the catheter 610 taken along lines 8b-8b in FIG. 8a. It is noted that 300-series reference numbers are used in FIGS. 8a-b to refer to like elements described above with reference to FIGS. 2a and 2b. Therefore the description of some elements may not be repeated in the discussion of FIGS. 8a-b.

The embodiment of catheter 310 shown in FIG. 8a-b is similar to the catheter 210 described above with reference to FIG. 6a-b, but instead of having at least two piezoelectric sensors, it has at least four piezoelectric sensors 316a-d. Each of the piezoelectric sensors is positioned eccentrically away from the central axis or neutral plane 336 of the catheter shaft 318 and in transverse planes relative to one another, as can be seen in FIG. 8b. In addition to detecting motion of the catheter, the relative magnitude and direction of the signal obtained from each of the four sensors may be also be used to determine the plane of deflection of the catheter 610. Each of the piezoelectric sensors 316a-d may be insulated by a compliant layer, which may also help distinguish the hydrodynamic condition.

FIG. 9a is a cross-sectional view of a portion of another exemplary catheter 410 with a piezoelectric sensor 416. FIG. 9b is a cross-sectional view of the catheter 410 taken along lines 9b-9b in FIG. 9a. FIG. 9c is a cross-sectional view of the catheter 410 taken along lines 9c-9c in FIG. 9a. It is noted that 400-series reference numbers are used in FIG. 9a-c to refer to like elements described above with reference to FIGS. 2a and 2b. Therefore the description of some elements may not be repeated in the discussion of FIG. 9a-c.

Catheter 410 may comprise a flexible catheter shaft 418 with at least one twisted piezoelectric sensor 416. In an exemplary embodiment, the piezoelectric sensor 416 is "quarter-twisted" (i.e. the front portion is rotated 90 degrees with respect to the back portion as shown in FIG. 9a) and positioned in the catheter shaft 418 along the central axis or neutral plane 436 of the catheter shaft 418. Use of a quarter-twisted piezoelectric sensor 416 that is positioned in the neutral plane 436 enables detection of symmetric voltage signals for equi-amplitude defections any direction about the neutral axis (e.g., as illustrated by arrows 440 and 441, and also into and out of the paper). That is, the amount of dynamic deflection in any direction is proportional to the amplitude of the voltage signal generated from the sensor 416.

Optionally, the piezoelectric sensor 416 is laminated to increase the sensitivity of the sensor 416. In addition, the piezoelectric sensor 416 may also be housed in a compliant section 434 of the catheter 410. The compliant section 434 acts as a low pass mechanical filter for the sensor and attenuates the high frequency noise signal when the catheter 410 moves in response to movement of the myocardial wall during intermittent contact.

FIG. 10a is a cross-sectional view of a portion of another exemplary catheter 510 with a piezoelectric sensor 516. FIG. 10b is a cross-sectional view of the catheter 510 taken along lines 10b-10b in FIG. 10a. FIG. 10c is a cross-sectional view of the catheter 510 taken along lines 10c-10c in FIG. 10a. It is noted that 500-series reference numbers are used in FIG. 10a-c to refer to like elements described above with reference to FIGS. 2a and 2b. Therefore the description of some elements may not be repeated in the discussion of FIG. 10a-c.

The embodiment of catheter 510 shown in FIG. 10a-c is similar to the catheter 410 described above with reference to FIG. 9a-c in that it comprises at least one twisted piezoelectric sensor 516, and similar to the catheter 110 described above with reference to FIG. 5a-b in that the piezoelectric sensor 516 is positioned eccentrically away from the central axis or neutral plane 536 of the catheter shaft 518. As already discussed above with reference to the catheter 310, the twisted piezoelectric sensor 516 enables detection of symmetric voltage signals for equi-amplitude defections any direction about the neutral axis. And as discussed above with regard to the catheter 110, the strain on the piezoelectric sensor 516 increases as it is positioned farther away from the neutral plane 536 of the catheter 510. This increased strain on the piezoelectric sensor 516 results in a higher amplitude signal from deflection of the catheter 510, and hence greater sensitivity when detecting motion.

FIG. 11a is a cross-sectional view of a portion of another exemplary catheter 610 with a piezoelectric sensor 616. FIG. 11b is a cross-sectional view of the catheter 610 taken along lines 11b-11b in FIG. 11a. FIG. 11c is a cross-sectional view of the catheter 610 taken along lines 11c-11c in FIG. 11a. It is noted that 600-series reference numbers are used in FIG. 11a-c to refer to like elements described above with reference to FIG. 2a and 2b. Therefore the description of some elements may not be repeated in the discussion of FIG. 11a-c.

The embodiment of catheter 610 shown in FIG. 11a-c is similar to the catheter 510 described above with reference to FIG. 10a-c but it has at least two piezoelectric sensors 616a-b positioned eccentrically away from the central axis or neutral plane 636 of the catheter shaft 618. The piezoelectric sensors 616a-b are positioned in a transverse plane relative to one another. In addition to detecting motion of the catheter, the relative magnitude and direction of the signal obtained from each of the two sensors may be also be used to determine the plane of deflection of the catheter 610.

Although several embodiments of this invention have been described above with a certain degree of particularity, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A contact sensing system for a catheter, the system comprising:
   a flexible catheter shaft;
   a compliant material inside the outside catheter wall;
   at least one piezoelectric sensor oriented coaxial to the flexible catheter shaft, the at least one piezoelectric sensor provided within a cavity in the compliant material, so that the at least one piezoelectric sensor is responsive to movement of the flexible catheter shaft by generating electrical signals corresponding to the amount of movement; and
   an output device electrically connected to the at least one piezoelectric sensor, the output device receiving the electrical signals for dynamically assessing a level of contact between a distal portion of the catheter and a moving tissue.

2. The system of claim 1, wherein the level of contact between the distal portion and the moving tissue corresponds to the electrical signals generated by the at least one piezoelectric sensor.

3. The system of claim 2, wherein the level of contact is proportional to the signal strength.

4. The system of claim 2, wherein the level of contact is proportional to amplitude of the electrical signals.

5. The system of claim 2, wherein the level of contact corresponds to periodicity of the electrical signals.

6. The system of claim 1, further comprising a compliant layer at least partially surrounding the at least one piezoelectric sensor, the compliant layer reducing noise effects from intermittent contact of the distal portion.

7. The system of claim 1, wherein the at least one piezoelectric sensor is housed within the distal portion.

8. The system of claim 1, wherein the at least one piezoelectric sensor is provided on an outer surface of the distal portion.

9. The system of claim 1, wherein the at least one piezoelectric sensor includes a piezoelectric material laminated to at least one protective layer.

10. The system of claim 1, wherein the at least one piezoelectric sensor includes a piezoelectric film.

11. The system of claim 1, further comprising a plurality of piezoelectric sensors.

12. The system of claim 11, wherein the plurality of piezoelectric sensors are oriented with a pole of each piezoelectric sensor facing an inner surface of the flexible catheter shaft, the plurality of piezoelectric sensors generating electrical signals for assessing the level of contact between the distal portion and the moving tissue in endoluminal flow conditions.

13. The system of claim 11, wherein the electrical signals generated by each of the piezoelectric sensors are substantially in-phase with one another if the distal portion is free-floating in a hydrodynamic environment.

14. The system of claim 11, wherein the electrical signals generated by each of the piezoelectric sensors are out-of-phase with one another if the distal portion is in contact with the moving tissue.

15. The system of claim 1, wherein the at least one piezoelectric sensor is quarter-twisted.

16. A method comprising:
generating piezoelectric signals in response to movement of a distal portion of a flexible catheter by at least one piezoelectric sensor provided within a compliant material inside the outer catheter wall in a cavity in the flexible catheter shaft; and
dynamically assessing a level of contact between the distal portion and a moving tissue based on the piezoelectric signals.

17. The method of claim 16, further comprising determining the level of contact based on strength of the piezoelectric signals.

18. The method of claim 16, further comprising determining the level of contact based on amplitude of the piezoelectric signals.

19. The method of claim 16, further comprising determining the level of contact based on periodicity of the piezoelectric signals.

20. The method of claim 16, further comprising reducing noise artifacts during distal portion movement.

21. The method of claim 16, further comprising reducing noise effects from intermittent contact of the distal portion.

22. The method of claim 16, further comprising generating simultaneous piezoelectric signals for assessing the level of contact between the distal portion and the moving tissue in endoluminal flow conditions.

23. The method of claim 22, further comprising:
comparing phase of the simultaneous piezoelectric signals;
determining that the distal portion is free-floating in a hydrodynamic environment if the simultaneous piezoelectric signals are in-phase with each other; and
determining that the distal portion is in contact with the moving tissue if the simultaneous piezoelectric signals are out-of-phase with each other.

24. The method of claim 16, further comprising detecting defections in any direction about a neutral axis of the flexible catheter.

25. The method of claim 16, further comprising determining a plane of deflection of the distal portion based on relative magnitude and direction of a signal obtained from each of two piezoelectric sensors in the distal portion.

26. A system for assessing catheter-tissue contact, comprising:
flexible means for applying ablative energy to a moving tissue;
means for generating piezoelectric signals corresponding to movement of the flexible means, the means for generating piezoelectric signals provided within a compliant material inside the outer catheter wall in a cavity in the flexible means; and
means for dynamically assessing a level of contact between the flexible means and the moving tissue based on the piezoelectric signals.

27. The system of claim 26, further comprising means for assessing the level of contact in endoluminal flow conditions.

28. The system of claim 26, further comprising means for reducing noise artifacts during distal portion movement.

29. The system of claim 26, further comprising means for reducing noise effects from intermittent contact of the flexible means.

30. The system of claim 26, further comprising means for detecting defections in any direction about a neutral axis of the flexible means.

31. The system of claim 26, further comprising means for determining a plane of deflection of the flexible means based on relative magnitude and direction of a signal obtained from each of two piezoelectric sensors in the flexible means.

32. The system of claim 1, wherein the cavity is insulated.

33. The system of claim 1, wherein the cavity is compliant.

34. A contact sensing system for a catheter, the system comprising:
a flexible catheter shaft;
one piezoelectric sensor oriented coaxial to the flexible catheter shaft, the one piezoelectric sensor responsive to movement of the flexible catheter in response to contact with an object external to the catheter shaft by generating electrical signals corresponding to the amount of movement detected at the piezoelectric sensor without any external input; and
an output device electrically connected to the one piezoelectric sensor, the output device receiving the electrical signals for dynamically assessing a level of contact between the a distal portion of the catheter and the external object.

* * * * *